(12) United States Patent
Li

(10) Patent No.: US 9,186,154 B2
(45) Date of Patent: Nov. 17, 2015

(54) PATIENT-SPECIFIC INSTRUMENTS FOR TOTAL ANKLE ARTHROPLASTY

(75) Inventor: Jia Li, Warsaw, IN (US)

(73) Assignee: ZIMMER, INC., Warsaw, IN (US)

( * ) Notice: Subject to any disclaimer, the term of this patent is extended or adjusted under 35 U.S.C. 154(b) by 30 days.

(21) Appl. No.: 13/050,190

(22) Filed: Mar. 17, 2011

(65) Prior Publication Data

US 2012/0239045 A1    Sep. 20, 2012

(51) Int. Cl.
| A61B 17/15 | (2006.01) |
| A61B 17/56 | (2006.01) |
| A61B 19/00 | (2006.01) |
| A61F 2/42 | (2006.01) |
| A61B 17/17 | (2006.01) |

(52) U.S. Cl.
CPC .............. *A61B 17/15* (2013.01); *A61B 17/157* (2013.01); *A61B 2017/1775* (2013.01); *A61B 2019/508* (2013.01); *A61F 2002/4205* (2013.01); *A61F 2002/4207* (2013.01)

(58) Field of Classification Search
CPC .... A61B 17/15; A61B 17/151; A61B 17/152; A61B 17/154; A61B 17/155; A61B 17/157; A61B 17/17; A61B 17/1717; A61B 17/1739; A61B 2017/1775; A61F 2/4202; A61F 2002/4205; A61F 2002/4207
USPC ........ 606/79, 82, 86 R, 87–89, 96; 623/21.18
See application file for complete search history.

(56) References Cited

U.S. PATENT DOCUMENTS

| 3,839,742 A | 10/1974 | Link |
| 3,872,519 A | 3/1975 | Giannestras et al. |
| 3,886,599 A | 6/1975 | Schlein |

(Continued)

FOREIGN PATENT DOCUMENTS

| WO | WO03/075802 A1 | 9/2003 |
| WO | WO2005/041823 A1 | 5/2005 |

(Continued)

OTHER PUBLICATIONS

International Search Report issued in corresponding International Patent Application No. PCT/US2012/027667, Apr. 24, 2012.

(Continued)

*Primary Examiner* — Kevin T Truong
*Assistant Examiner* — Tracy Kamikawa
(74) *Attorney, Agent, or Firm* — Norton Rose Fulbright Canada LLP

(57) ABSTRACT

Patient-specific instruments for preparing bones for receipt of orthopedic prostheses, such as the distal tibia and the talus in a total ankle arthroplasty (TAA) procedure. A tibial guide and a talar guide are manufactured based on patient-specific anatomical data obtained using imaging technology, and each guide includes a surface conforming to selected anatomical surfaces or regions of the tibia or talus, respectively. Each guide includes at least one cut referencing surface, such as a cut slot, to guide a resection, and may also include a guide aperture sized to guide a reaming tool for reaming the distal tibia or talus. The guides may also include pin holes positioned within a periphery defined by the cut referencing surfaces such that, when the resections are made and the resected tibial bone portion or talus bone portion is removed, the guide and its associated pins are removed along with the resected bone portion.

8 Claims, 13 Drawing Sheets

(56) References Cited

U.S. PATENT DOCUMENTS

| | | | |
|---|---|---|---|
| 3,889,300 | A | 6/1975 | Smith |
| 3,896,502 | A | 7/1975 | Lennox |
| 3,896,503 | A | 7/1975 | Freeman et al. |
| 3,975,778 | A | 8/1976 | Newton, III |
| 3,987,500 | A | 10/1976 | Schlein |
| 4,021,864 | A | 5/1977 | Waugh |
| 4,069,518 | A | 1/1978 | Groth, Jr. et al. |
| 4,156,944 | A | 6/1979 | Schreiber et al. |
| 4,232,404 | A | 11/1980 | Samuelson et al. |
| 4,470,158 | A | 9/1984 | Pappas et al. |
| 4,755,185 | A | 7/1988 | Tarr |
| 5,326,365 | A | 7/1994 | Alvine |
| 5,766,259 | A | 6/1998 | Sammarco |
| 5,768,134 | A | 6/1998 | Swaelens et al. |
| 5,824,106 | A | 10/1998 | Fournol |
| 6,409,767 | B1 | 6/2002 | Perice et al. |
| 6,663,669 | B1 | 12/2003 | Reiley |
| 6,852,130 | B2 | 2/2005 | Keller et al. |
| 6,860,902 | B2 | 3/2005 | Reiley |
| 6,863,691 | B2 | 3/2005 | Short et al. |
| 6,926,739 | B1 | 8/2005 | O'Connor et al. |
| 6,939,380 | B2 | 9/2005 | Guzman |
| 7,011,687 | B2 | 3/2006 | Deffenbaugh et al. |
| 7,025,790 | B2 | 4/2006 | Parks et al. |
| 7,323,012 | B1 | 1/2008 | Stone et al. |
| 7,485,147 | B2 | 2/2009 | Pappas et al. |
| 7,534,246 | B2 | 5/2009 | Reiley et al. |
| 7,534,270 | B2 | 5/2009 | Ball |
| 7,625,409 | B2 | 12/2009 | Saltzman et al. |
| 7,717,920 | B2 | 5/2010 | Reiley |
| 2003/0181985 | A1 | 9/2003 | Keller et al. |
| 2003/0204265 | A1 | 10/2003 | Short et al. |
| 2004/0002768 | A1 | 1/2004 | Parks et al. |
| 2004/0039394 | A1 | 2/2004 | Conti et al. |
| 2004/0117027 | A1 | 6/2004 | Reiley |
| 2004/0122523 | A1 | 6/2004 | Guzman |
| 2004/0133282 | A1 | 7/2004 | Deffenbaugh et al. |
| 2004/0167631 | A1 | 8/2004 | Luchesi et al. |
| 2004/0186585 | A1 | 9/2004 | Feiwell |
| 2005/0004676 | A1 | 1/2005 | Schon |
| 2005/0010232 | A1 * | 1/2005 | Crofford .......... 606/89 |
| 2005/0049711 | A1 | 3/2005 | Ball |
| 2005/0125070 | A1 | 6/2005 | Reiley |
| 2005/0182492 | A1 | 8/2005 | Pappas et al. |
| 2005/0288792 | A1 | 12/2005 | Landes et al. |
| 2006/0020345 | A1 | 1/2006 | O'Connor et al. |
| 2006/0142870 | A1 | 6/2006 | Robinson et al. |
| 2006/0229730 | A1 | 10/2006 | Railey et al. |
| 2006/0247788 | A1 | 11/2006 | Ross |
| 2007/0027547 | A1 | 2/2007 | Rydell et al. |
| 2007/0112431 | A1 | 5/2007 | Kofoed |
| 2007/0112432 | A1 | 5/2007 | Reiley |
| 2008/0065227 | A1 | 3/2008 | Reiley |
| 2008/0097617 | A1 | 4/2008 | Fellinger et al. |
| 2008/0275452 | A1 | 11/2008 | Lang et al. |
| 2008/0287954 | A1 | 11/2008 | Kunz et al. |
| 2009/0082875 | A1 | 3/2009 | Long |
| 2009/0105840 | A1 | 4/2009 | Reiley |
| 2009/0157083 | A1 | 6/2009 | Park et al. |
| 2009/0182433 | A1 | 7/2009 | Reiley et al. |
| 2009/0240338 | A1 | 9/2009 | Reiley |
| 2010/0262150 | A1 | 10/2010 | Lian |

FOREIGN PATENT DOCUMENTS

| | | |
|---|---|---|
| WO | WO2007/084846 A2 | 7/2007 |
| WO | WO2008/078082 A2 | 7/2008 |
| WO | WO2009015009 A1 | 1/2009 |
| WO | WO2009158522 A1 | 12/2009 |
| WO | WO2010/039026 A1 | 4/2010 |

OTHER PUBLICATIONS

Surgical Technique—Agility LP Total Ankle System, DePuy Orthopaedics, Inc. 2007.

Surgical Pocket Guide—Inbone Total Ankle System, Wright Medical Technology, Inc., date unknown, at least as early as Mar. 17, 2011.

Surgical Technique—Inbone Total Ankle System, Plus Size Poly Inserts, Wright Medical Technology, Inc. 2009.

Surgical Technique—Inbone Total Ankle System, Wright Medical Technology, Inc., date unknown, at least as early as Mar. 17, 2011.

* cited by examiner

FIG_9

FIG_10

PATIENT-SPECIFIC INSTRUMENTS FOR TOTAL ANKLE ARTHROPLASTY

BACKGROUND

1. Field of the Disclosure

The present disclosure relates to instruments for performing a total ankle arthroplasty (TAA) procedure. More particularly, the present disclosure relates to patient-specific instruments for use in a total ankle arthroplasty procedure.

2. Description of the Related Art

A total ankle arthroplasty (TAA) procedure may be performed to repair the diseased or damaged bone and/or cartilage of an ankle joint. In the procedure, a surgeon may use standard instruments to prepare the damaged joint for receiving an orthopedic prosthesis set.

For example, during a total ankle arthroplasty procedure, the surgeon may resect and/or ream the distal tibia to prepare the distal tibia for receiving a distal tibial prosthesis, and may also resect and/or ream the talus to prepare the talus for receiving a talar prosthesis. The distal tibial prosthesis typically includes an articulating surface that may be designed to articulate with respect to the talar prosthesis.

Known TAA procedures have required relatively complex instrumentation, including an alignment foot brace. Use of such a foot brace requires a bore to be drilled through the base of the heel bone, which extends completely through the heel and the talus and into the distal tibia. This bore is used to locate a referencing rod to which an instrument set is keyed, with the instrument set including a relatively large number of components, such as alignment guides and cut guides which interface with the referencing rod and/or the foot brace.

SUMMARY

The present disclosure provides patient-specific instruments for preparing bones for receipt of orthopedic prostheses, such as the distal tibia and the talus in a total ankle arthroplasty (TAA) procedure. A tibial guide and a talar guide are manufactured based on patient-specific anatomical data obtained using imaging technology, and each guide includes a surface conforming to selected anatomical surfaces or regions of the tibia or talus, respectively. Each guide includes at least one cut referencing surface, such as a cut slot, to guide a resection, and may also include a guide aperture sized to guide a reaming tool for reaming the distal tibia or talus along the anatomical axis of the distal tibia or for preparing transverse holes to receive an implant. The guides may also include pin holes positioned within a periphery defined by the cut referencing surfaces such that, when the resections are made and the resected tibial bone portion or talus bone portion is removed, the guide and its associated pins are removed along with the resected bone portion. The guides may be designed to ensure that a proximal resected surface of the distal tibia is parallel to a resected surface of the talus, with the parallel resected surfaces perpendicular to the anatomical axis of the distal tibia.

According to an embodiment of the present disclosure, a tibial guide for preparing a distal tibia to receive a prosthesis includes a body having a first portion including a patient-specific surface being contoured to rest against and substantially conform to one or more portions of at least one of an articular capsule, an anterior protrusion, and a medial malleolus of the distal tibia.

According to another embodiment of the present disclosure, a talar guide for preparing a talus to receive a prosthesis includes a body including a first portion including a patient-specific surface being contoured to rest against and substantially conform to one or more portions of at least one of a proximal surface, a medial edge, and a lateral edge of a trochlea of a talus.

According to yet another embodiment of the present disclosure, a patient-specific guide for guiding an instrument to resect a resection portion of a bone to prepare the bone to receive a prosthesis includes a body having a patient-specific referencing portion and a resection guide portion, the referencing portion including at least one patient-specific surface being contoured to rest against and substantially conform to a surface of the bone, the resection guide portion including at least one cut referencing surface defining at least a portion of a periphery of the resection portion of the bone, and the body further including at least one pin aperture disposed in at least one of the referencing portion and the resection guide portion, each pin aperture disposed within the periphery of the resection portion of the bone when the patient-specific surface is conformingly positioned against the bone, each pin aperture dimensioned to receive a pin to secure the guide to the bone.

BRIEF DESCRIPTION OF THE DRAWINGS

The above-mentioned and other features and advantages of this disclosure, and the manner of attaining them, will become more apparent and the disclosure itself will be better understood by reference to the following description of embodiments of the disclosure taken in conjunction with the accompanying drawings, wherein.

Corresponding reference characters indicate corresponding parts throughout the several views. The exemplifications set out herein illustrate exemplary embodiments of the disclosure and such exemplifications are not to be construed as limiting the scope of the disclosure in any manner.

DETAILED DESCRIPTION

Figure 14:
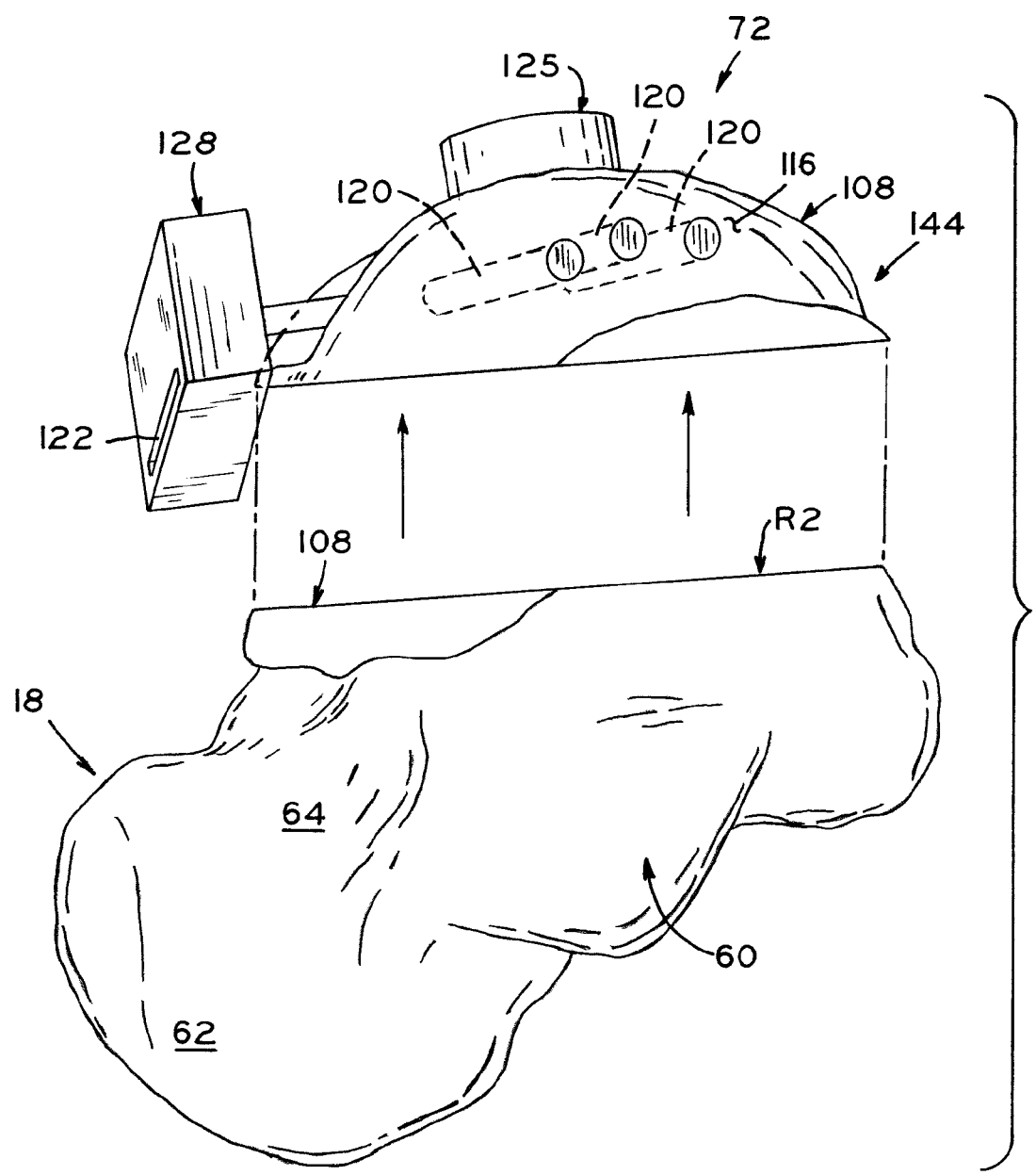
FIG. 14 is a lateral perspective view of the talar guide of FIG. 7 being removed along with a resected portion of the talus after performing the resection.
Figure 15:
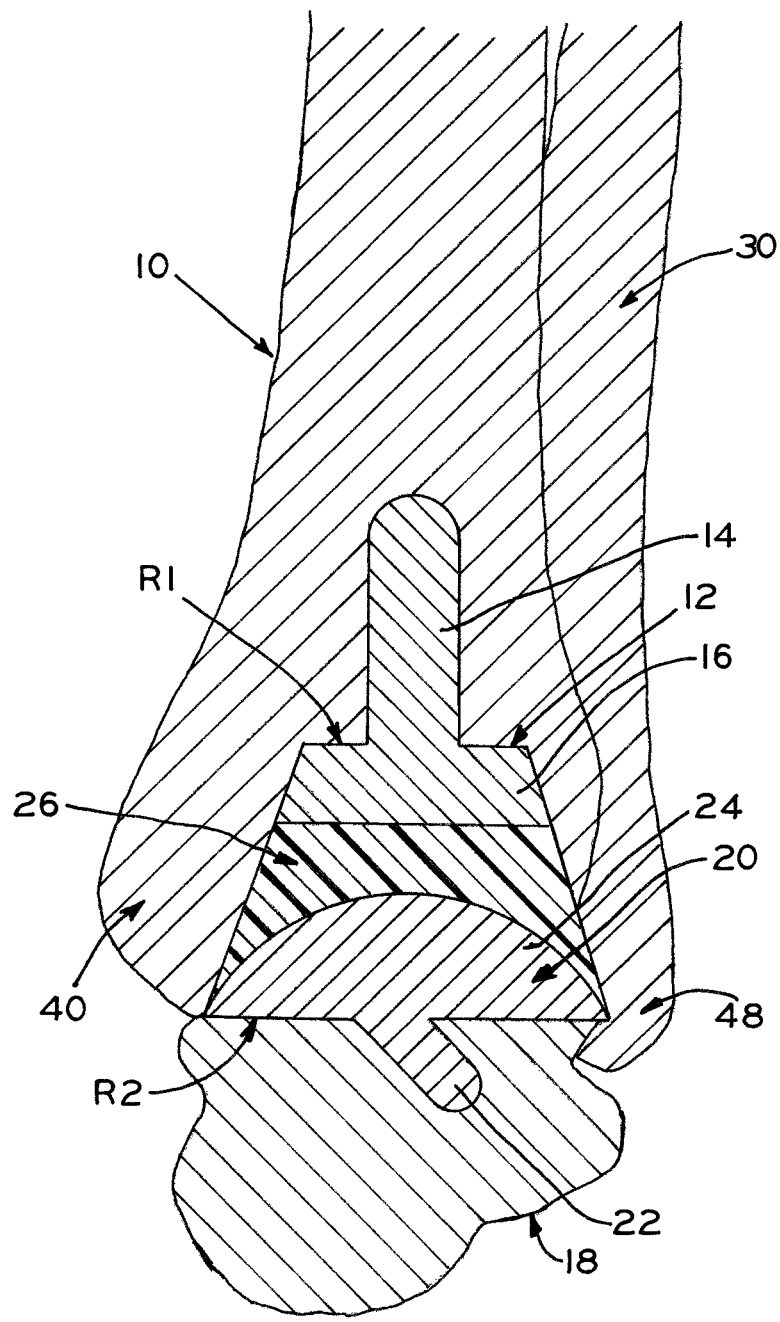
FIG. 15 is a cross-sectional anterior view of an ankle joint, showing the placement of an exemplary set of orthopedic prostheses.

An orthopedic instrument system of FIGS. 1-15 is provided for preparing distal tibia 10 (FIGS. 1-3) to receive a distal tibial prosthesis and for preparing talus 18 (FIGS. 1, 2 and 4) to receive a proximal talar prosthesis, such that the prostheses, when implanted, articulate against one another to restore mobility to the ankle joint. For example, as shown in FIG. 15, exemplary tibial prosthesis 12 includes stem component 14 and head component 16, and exemplary talar prosthesis 20 includes stem component 22 and head component 24. The head components of the distal tibial prosthesis and the proximal talar prosthesis articulate with one another, either directly or via an optional polymer insert 26 disposed between these components. In an exemplary embodiment, the tibial and talar prostheses are those described in U.S. Pat. No. 7,625,409 or U.S. Patent Application Publication No. 2005/0004676, both of which are hereby expressly incorporated herein by reference.

Although the present orthopedic instrument system is described and depicted herein as being used to prepare tibia 10 and talus 18 in connection with a total ankle arthroplasty ("TAA") procedure, the orthopedic system may be modified for use to prepare other anatomical structures, such as the humerus, scapula, femur, proximal tibia, radius, ulna, and other bones, to receive corresponding orthopedic prostheses.

Figure 1:
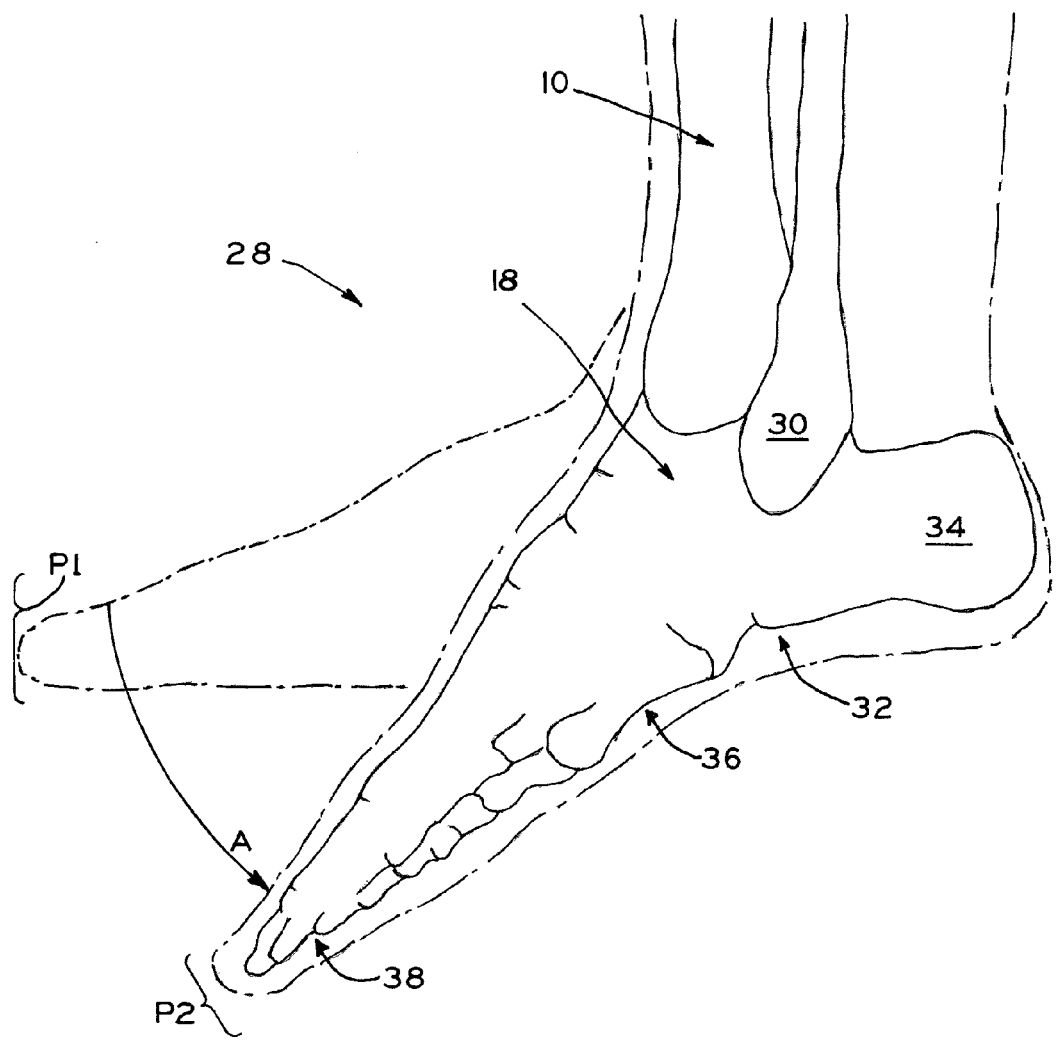
FIG. 1 is an elevational view showing the bones of an ankle joint.

As shown in FIG. 1, the left foot 28 includes distal tibia 10 laterally adjacent fibula 30, with distal tibia 10 and fibula 30 articulating against talus 18 of tarsus 32 of foot 28. Tarsus 32 includes the following bones: calcaneous 34, talus 18, cuboid (not shown), navicular (not shown), and lateral, medial, and intermediate cuneiforms (not shown). Tarsus 32 of foot 28 articulates with metatarsus 36, which in turn articulates with phalanges 38, or toe bones. Foot 28 may pivot in the direction of arrow A of FIG. 1 about the ankle joint formed between tibia 10, fibula 30, and tarsus 32 (particularly, talus 18) to move from a first position shown as position P1 to a second position shown as position P2.

Figure 3:
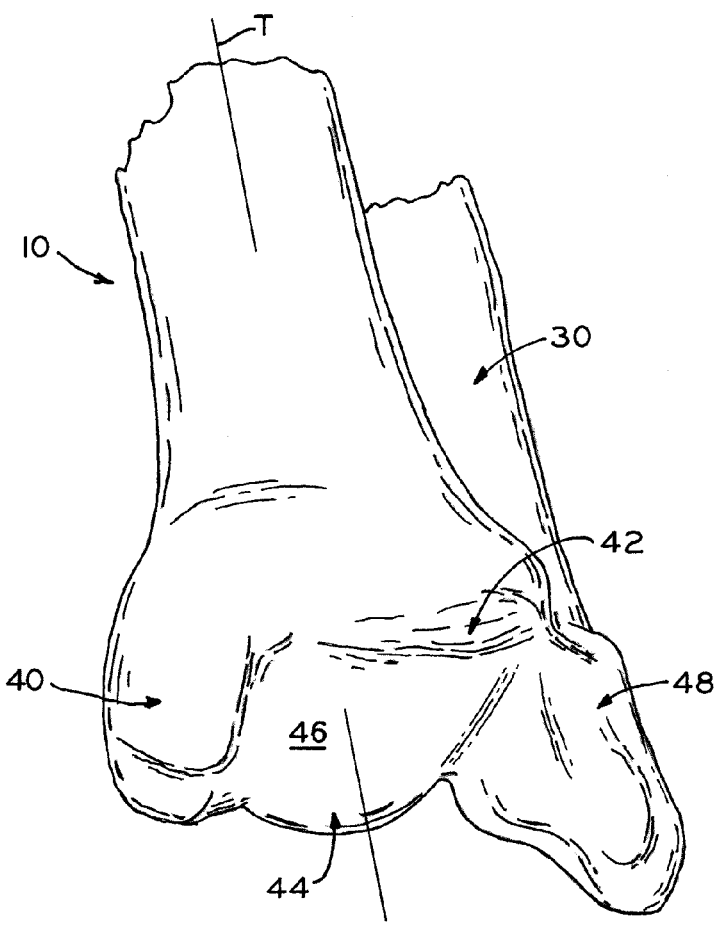
FIG. 3 is a distal perspective view of the distal tibia showing the distal surfaces of the distal tibia.

As shown in FIG. 3, the distal end of tibia 10 includes medial malleolus 40, anterior protrusion 42, posterior protrusion 44, and concave articular capsule 46 defined by medial malleolus 40, anterior and posterior protrusions 42 and 44, and lateral malleolus 48 of fibula 30, which is disposed laterally adjacent tibia 10. While the figures and discussion herein reference the ankle joint of the left leg, the present disclosure applies to the ankle joint of the right leg as well. Once tibia 10 is prepared, as further described below, a distal tibial prosthesis such as prosthesis 12 of FIG. 16 is inserted into the prepared distal tibia along the anatomical axis T of the distal tibia.

Figure 4:
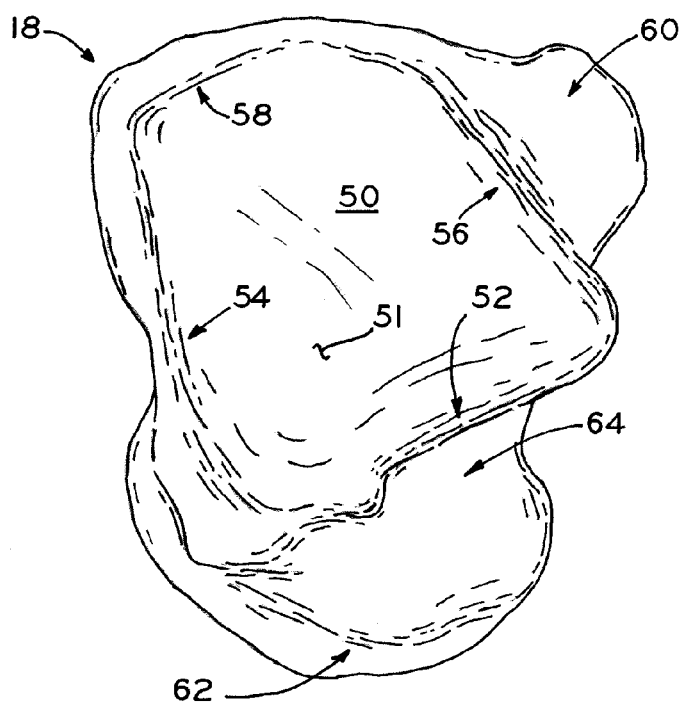
FIG. 4 is a proximal plan view of the talus.

As shown in FIG. 4, talus 18 includes talar dome or trochlea 50, which is the convex proximal surface of talus 18 for articulation with concave articular capsule 46 of distal tibia 10. Particularly, trochlea 50 includes a proximal surface 51, anterior surface 52, posterior surface 58, and medial and lateral edges 54 and 56. Trochlea 50 tapers from a broader anterior surface 52 along medial and lateral edges 54 and 56 towards a narrower posterior surface 58. Lateral edge 56 of trochlea 50 is disposed above a groove for receiving lateral malleolus 48 of fibula 30, and medial edge 54 of trochlea 50 is disposed above a groove for receiving medial malleolus 40 of distal tibia 10. Talus 18 further includes lateral tubercle 60, and head 62 connected to trochlea 50 via neck 64.

1. Case Planning

As described further below, patient-specific images taken of the ankle joint anatomy are used to create patient-specific guides conforming to landmarks of the anatomy. Once appropriately placed on and conforming to the landmarks that indicate a desired positioning, the guides assist to prepare the talus and distal tibia for receiving their respective implants in a desired position and orientation.

Figure 5:
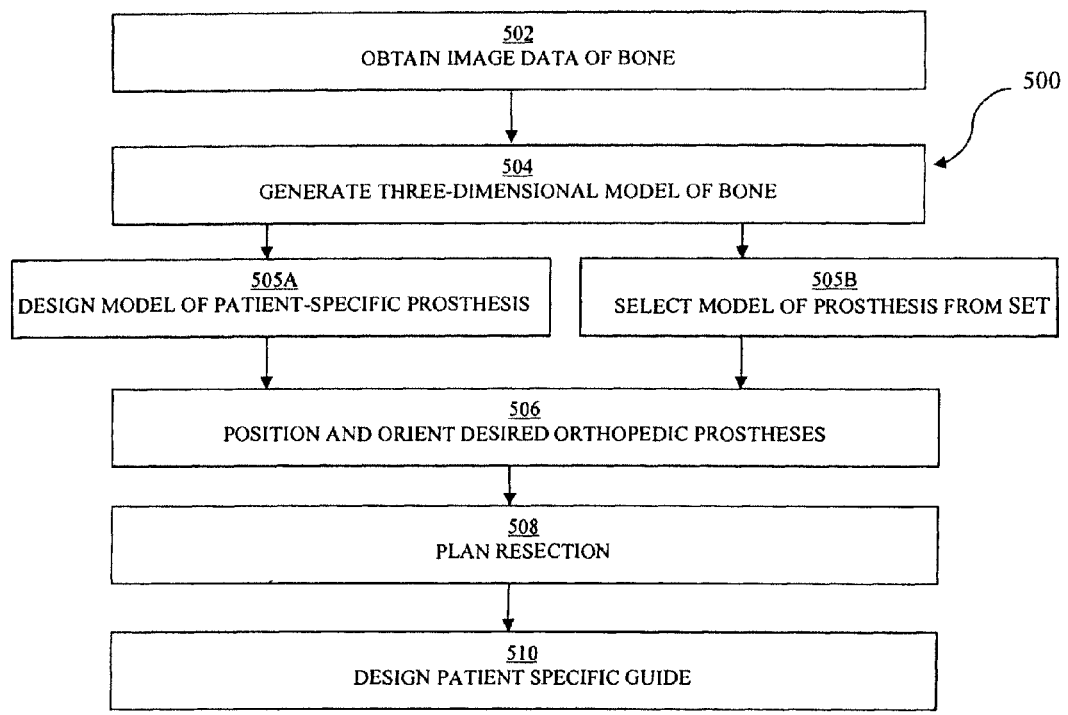
FIG. 5 is a flow chart of an exemplary method of the present disclosure.

Referring to FIG. 5, an exemplary method 500 is provided for designing, manufacturing, and using a patient-specific tibial guide, such as tibial guide 70 of FIG. 6, described further below, to prepare a distal end of tibia 10 (FIG. 3) and a patient-specific talar guide, such as talar guide 72 of FIG. 7, described further below, to prepare a proximal end of talus 18 (FIG. 4).

First, in step 502 of method 500, the surgeon obtains image data of a patient's ankle joint, including a distal end of tibia 10 and a proximal end of talus 18, using a suitable imaging modality, such as magnetic resonance imaging (MRI), computed tomography (CT), X-ray, ultrasound, or any another suitable imaging technique by which a volumetric, three dimensional image data set of the patient's joint may be obtained or calculated. For example, joint data may be obtained and manipulated as described in U.S. Pat. No. 5,768,134, entitled Method for Making a Perfected Medical Model on the Basis of Digital Image Information of a Part of the Body, issued Jun. 16, 1998, the entirety of which is hereby incorporated by reference herein. The imaging modality may further utilize a gantry tilt technology to obtain scans. The gantry tilt technology allows for alignment between a selected anatomic region and a scanning plane that is angled against a vertical plane.

Optionally, as shown FIG. 1, the patient's ankle joint may be placed in extension and/or flexion prior to obtaining the imaging data. In many patients who have arthritis or another disease or condition that affects the ankle joint, it may be helpful for the surgeon to assess the joint space between the distal end of tibia 10 and the proximal end of talus 18 in tension to properly size the associated orthopedic prostheses and to optimally reconstruct the ankle joint. A suitable brace (not shown) may be applied to pull on the ankle, for example, in order to place the ankle joint in tension. In this manner, when the imaging data is obtained, tibia 10, talus 18, and the surrounding soft tissue are all visible about the joint space such that the surgeon may evaluate soft tissue laxity to properly determine the size and position of the orthopedic prostheses, as discussed further below.

In addition to obtaining three dimensional imaging data of the ankle joint when the ankle is in extension, shown as position P1 of FIG. 1, further imaging data may also be obtained of the ankle joint in flexion, such as in mid flexion shown as position P2 in FIG. 1, or in about 45° flexion. In one embodiment, additional three dimensional volumetric scans may be obtained in each of the foregoing positions. Alternatively, a two-dimensional imaging modality, such as an X-ray or fluoroscopy, may be used to obtain additional images in one or more positions in which the ankle joint is in flexion, and a tension brace of the type described above may be used to assess laxity in the joint space. As described below, this additional imaging data may be used to construct a computer model of the ankle joint and/or aid in the determination of the size and positioning of the orthopedic prostheses. For example and similarly as described above, joint data may be obtained and manipulated as described in U.S. Pat. No. 5,768,134, incorporated by reference above.

Next, in step 504 of method 500, the imaging data of tibia 10 and talus 18 obtained during step 502 may be processed by a computer planning system which includes suitable computer software to generate a three-dimensional computer model of tibia 10, talus 18, and, if desired, the upper leg and the contralateral leg. For example, the computer planning system may include image processing software that is able to segment, or differentiate, relatively dense anatomic structure (e.g., bone tissue) from less dense structures (e.g., the surrounding soft tissue in the joint). Then, the image processing software generates a computer model of the desired structure. One suitable method for generating a computer model of a desired anatomic structure involves assigning a grey value to each pixel of the imaging data, setting a threshold grey value, and segmenting desired pixels from undesired pixels based on the threshold grey value. Another suitable method relies on using the density information gathered from the MRI or CT scans.

Using the computer model from step 504, the surgeon then selects a model of each desired prosthesis, for example, the desired tibial and talus prostheses. The prostheses may include modular components such as, for example, a head and a stem component. According to an exemplary embodiment of the present disclosure, the computer planning system displays the computer model to the surgeon so that the surgeon can evaluate the anatomy of the joint to determine the implant solution that is optimized for the anatomical needs of the patient. Selecting the model of each desired prosthesis may involve designing a custom, patient-specific prosthesis in step 505A of method 500 or choosing a standard prosthesis from a set of known orthopedic prostheses in step 505B of method 500. For example, in step 505A, the surgeon or computer planning system may design a model of a patient-specific implant that best matches the anatomical needs of the patient. Alternatively, in step 505B, the surgeon or computer planning system may access a digital database or library of known or "standard" orthopedic prostheses, and select a model of a desired prosthesis from the database.

Then, in step 506 of method 500, the surgeon may use the computer model of tibia 10 and talus 18 to position and orient the selected orthopedic prostheses from step 505 relative to the bones. It is within the scope of the present disclosure that the orienting and positioning step 506 may occur after or simultaneously with the selecting step 505. According to an exemplary embodiment of the present disclosure, the surgeon overlays a digital representation or image of the desired prostheses onto the computer model of the associated bone to ensure the proper size of the desired prostheses and the proper orientation of the desired prostheses relative to the associated bone.

In certain embodiments, the surgeon or computer planning system may evaluate soft tissue laxity to properly size multiple prostheses simultaneously. For example, the computer planning system may evaluate soft tissue laxity in the ankle joint to simultaneously size a distal tibial prosthesis (such as prosthesis 12 of FIG. 16) and a proximal talus prosthesis (such as prosthesis 20 of FIG. 16). Also, if multiple data sets of the ankle joint in various positions of extension and flexion have been obtained, the same may be used for modelling a dynamic representation of the joint in which the surgeon may assess the joint in multiple positions of extension and flexion.

After the surgeon plans the size and location of the desired prostheses using the computer model during step 506, the computer planning system determines at step 508 of method 500 which portions of the bone must be removed from the computer model to receive the desired prostheses. In one embodiment, the computer planning system may identify for removal areas of overlap between the computer model of the bone and the digital model of the desired prostheses.

For example, using the computer model of the bone and the digital model of the desired prostheses, the computer planning system may determine that a cavity must be formed into the tibial canal superiorly through a distal-inferior surface of tibia 10 along the longitudinal or anatomical axis T of distal tibia 10, which is located based on imaging data. As further described below, a reaming guide aperture for the tibial resection guide is located based on the determined anatomical axis of the distal tibia (FIG. 2) to ream a tibial canal along the anatomical axis. The system may also determine the locations of proximal, medial, and lateral resection planes along which resections are to be made to distal tibia 10.

Figure 2:
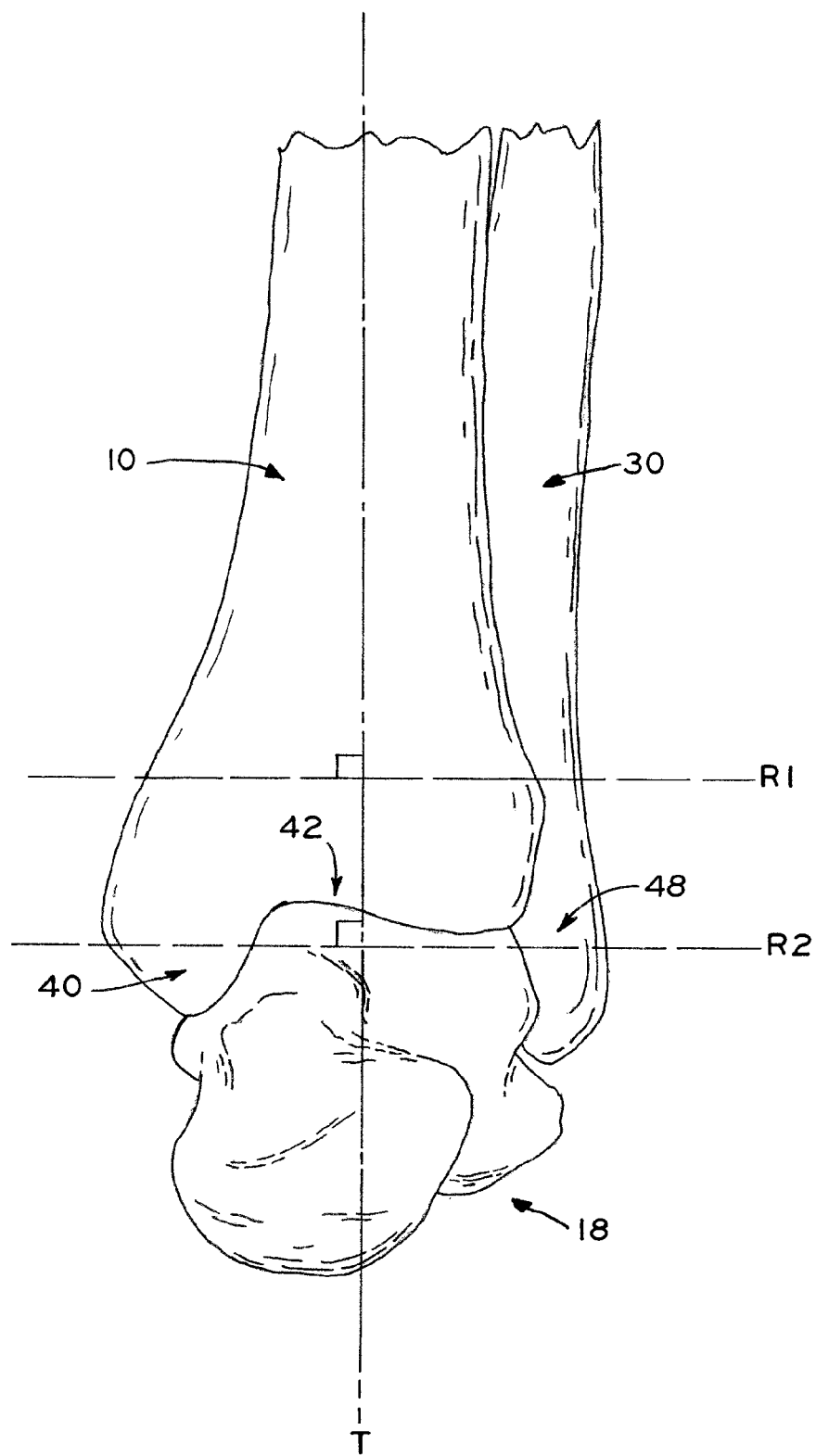
FIG. 2 is an anterior fragmentary view of the bones of the ankle joint of FIG. 1, showing the talus bone in articulation with the distal tibia and fibula, the anatomical tibial axis, and two parallel resection planes associated with the distal tibia and talus, respectively, which are aligned normal to the anatomical tibial axis.

Additionally, as shown in FIG. 2, a proximal resection is made along a resection plane R1 that is planned to be perpendicular to anatomical axis T of tibia 10 and of the associated reamed tibial canal. The tibial proximal resection acts as a referencing surface for a tibial prosthesis.

In addition, the system may determine that talus 18 must be reamed to a desired depth in preparation to receive a stem component of a proximal talus prosthesis, and that a resection must be made of a proximal end of talus 18 along a determined proximal resection plane R2, as shown in FIG. 2, that is parallel to the determined proximal resection plane R1 of tibia 10 and perpendicular to anatomical axis T of tibia 10. The talar proximal resection acts as a referencing surface for a talar prosthesis.

Next, in step 510 of method 500 of FIG. 5, the computer planning system is used to design a custom, patient-specific guide, such as guide 70 for tibia 10 (FIGS. 6 and 8) and/or guide 72 for talus 18 (FIG. 7) based on the calculations from step 508. Each patient-specific guide may be an entirely custom product that is manufactured using a rapid prototyping process, such as 3-D printing, stereolithography, selective laser sintering, fused deposition modeling, laminated object manufacturing, or electron beam melting, for example. Alternatively, each patient-specific guide may be manufactured by removing material from a near net-shape blank or standard guide. Some or all of the steps of method 500 described herein may involve an online management system and/or a digital templating system.

2. Surgical Guides

The exemplary surgical guides of the present disclosure, such as an exemplary tibial guide 70 and an exemplary talar guide 72, described below, are designed in accordance with the methods discussed above.

Each of the tibial guide and the talar guide includes at least one surface conforming to selected anatomic surfaces or regions of the tibia or talus, respectively. Each guide may also include instrument guidance features such as at least one cut referencing surface to guide a cutting instrument for resecting a tibial portion of the distal tibia or a proximal portion of the proximal talus, and a reaming guide aperture sized to guide a reaming tool for reaming a canal portion of the distal tibia or talus, respectively, based on the anatomical axis of the distal tibia or for reaming transverse holes perpendicular to the anatomical axis of the tibia to prepare the bone for an implant with anchor portions extending from medial to lateral edges of the tibia and/or talus.

Each of the guides described herein may be temporarily secured into position with fasteners such as pins, screws, and like devices. In particular, pin holes may be positioned within a periphery defined by the cut referencing surfaces such that, when the tibial bone portion or the talus bone portion is removed, the guide and associated pins securing the respective guide to the bone are simultaneously removed with the resected bone. Further, the guides will guide the formation of parallel resections of the distal tibia and proximal talus such that the parallel resected surfaces are perpendicular to the anatomical axis of the distal tibia.

Advantageously, the exemplary guides of the present disclosure, as described further below, facilitate the preparation of the distal tibia and proximal talus for receiving a respective prosthesis according to a desired alignment without the need for a foot brace or other complex instrumentation typically used with known total ankle replacement procedures. Further advantageously, in using the exemplary guides of the present disclosure, there is no need to drill a bore through a base of the heel bone and upwards through the heel and the talus and into the distal tibia, as is typical in prior procedures.

In an alternative embodiment, each of the tibial and/or talus guides of the present disclosure may include pin guide holes through which holes may be drilled for use in locating and placing pins onto the respective bone. The respective tibial and/or talus guide may then be removed and a separate cut guide, which may be either a patient specific cut guide or a non-patient specific cut guide, may be fitted over the placed pins. Thus, the pins assist with locating the cut guide into a desired position with the respective bone. After a resection is made, the cut guide may be removed from the bone. The pins may or may not be within the periphery of the resection, and thus respectively may or may not be removed with the resected portion of bone.

2A. Tibial Guide (FIGS. 6 and 8-11)

Referring to FIGS. 6 and 8-11, an exemplary tibial guide 70 of the present orthopedic instrument system includes a first, patient-specific referencing portion 74 that includes proximal surface 76 (FIG. 8) that substantially conforms to and is a negative of surfaces and/or landmarks of the distal tibia along at least one of medial malleolus 40, anterior protrusion 42, and articular capsule 46. Typically, proximal surface 76 of referencing portion 74 will be shaped to conform and seat against anterior protrusion 42 of distal tibia 10, though seating against posterior protrusion 44 of distal tibia 10 is also possible. Further, proximal surface 76 of referencing portion 74 and/or extensions from proximal surface 76 may conform to patient-specific deformities and/or irregularities in distal tibia 10.

Figure 8:
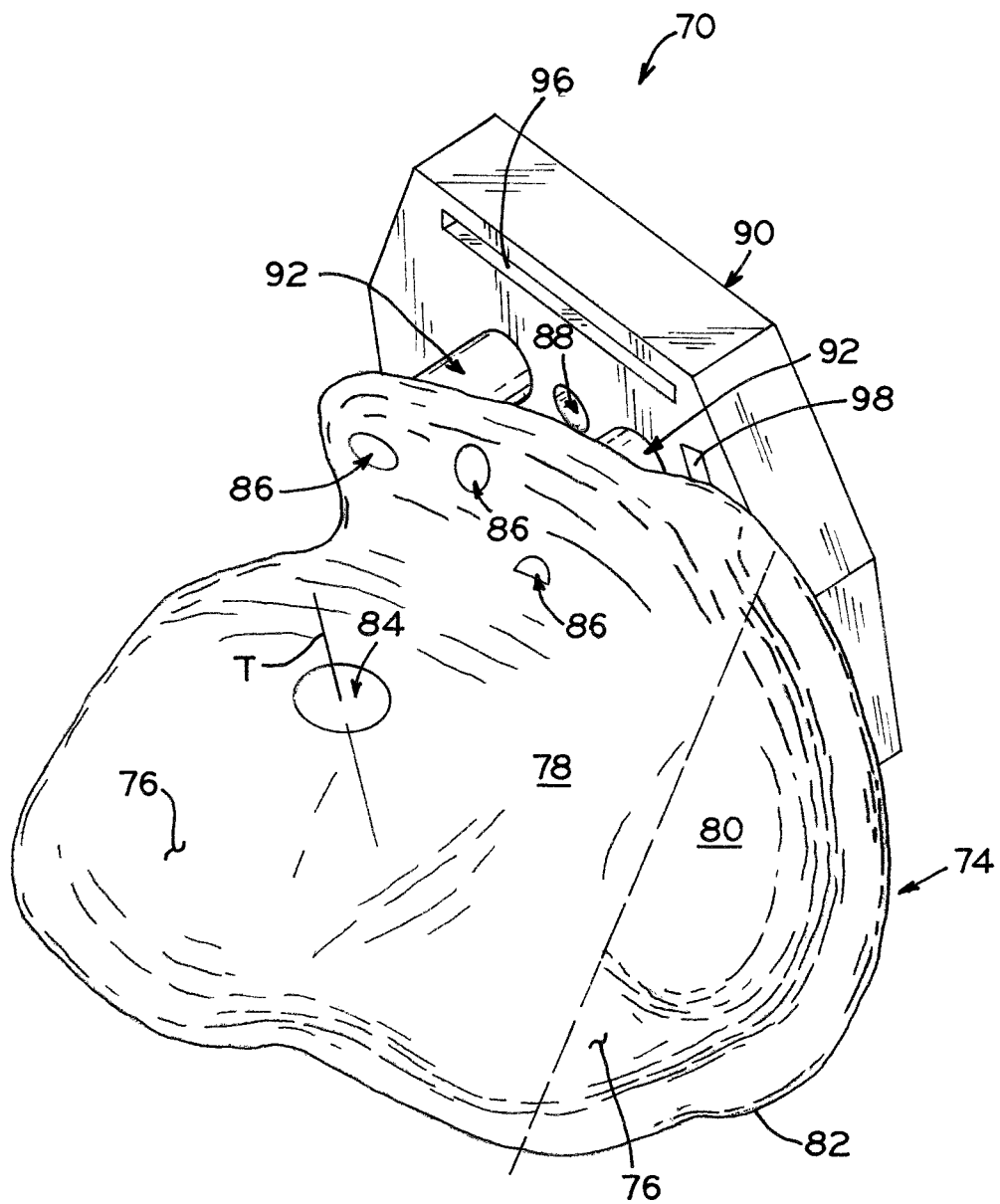
FIG. 8 is a proximal perspective view of the tibial guide, including a referencing portion and a resection guide portion, the referencing portion having a reaming guide aperture and a proximal patient-specific surface for conforming and seating to distal surfaces of the distal tibia, the resection guide portion including cut slots.

Referring to FIG. 8, referencing portion 74 includes first and second portions 78 and 80, proximal surface 76, and distal surface 82 opposite proximal surface 76. First portion 78 includes the portion of proximal surface 76 of referencing portion 74 that substantially conforms to and is a negative of selected regions or portions of anterior protrusion 42 and articular capsule 46 of distal tibia 10 (FIG. 3). First portion 78 of referencing portion 74 includes reaming guide aperture 84 extending between proximal surface 76 and distal surface 82 of referencing portion 74. Reaming guide aperture 84 may optionally be formed through a boss 83 (FIG. 6) distally extending from distal surface 82.

Guide aperture 84 of referencing portion 74 is designed based on patient-specific imaging data to align with anatomical axis T of distal tibia 10 when referencing portion 74 is seated against distal tibia 10. Guide aperture 84 may guide an instrument such as reamer 85 of FIG. 9 to ream the tibial canal along the anatomical axis, as described further below.

First portion 78 of referencing portion 74 includes pin apertures 86 that are positioned to align with pin apertures 88 (FIGS. 8-10) of second, resection guide portion 90 (FIG. 6), discussed further below.

Second portion 80 of referencing portion 74 includes the portion of proximal surface 76 of referencing portion 74 that substantially conforms to and is a negative of selected regions of anterior protrusion 42 and medial malleolus 40 of distal tibia 10 (FIG. 3).

Referencing portion 74 of guide 70 is connected to second, resection guide portion 90, which may be integral with or modular and separately attached to referencing portion 74. For example, shafts 92 shown in FIG. 8 may connect resection guide portion 90 to referencing portion 74. Aperture 86 of referencing portion 74 and an aperture 88 of second resection guide portion 90 (FIG. 6) are sized to receive a pin such as pin 94 (FIG. 10) to attach guide 70 to bone when guide 70 is seated against distal tibia 10. In an alternative embodiment, apertures may extend continuously through both resection guide portion 90 and referencing portion 74.

Figure 9:
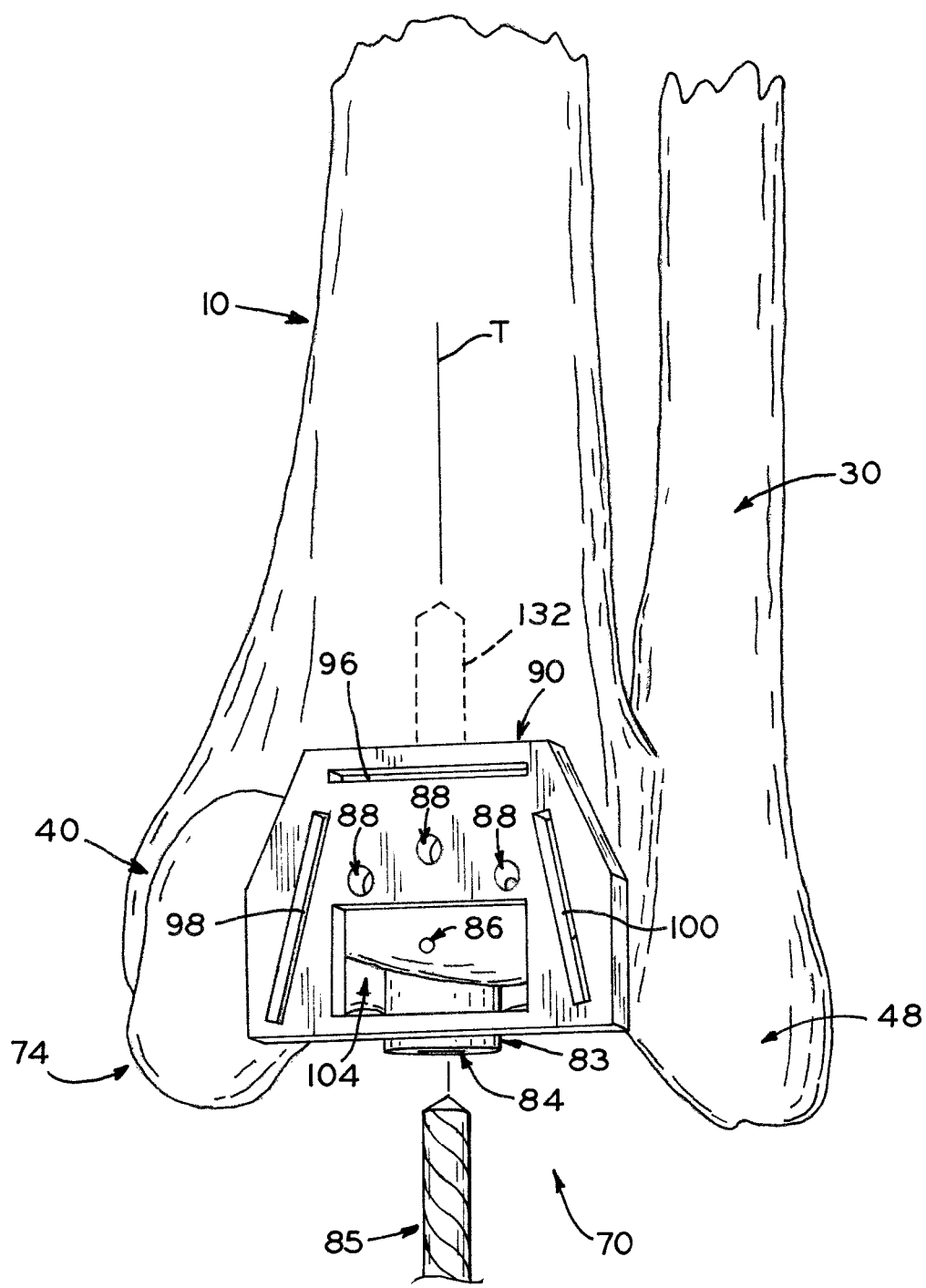
FIG. 9 is an anterior view of the tibial guide of FIG. 8 seated on the distal tibia, showing a reaming instrument guided via the reaming guide aperture of the referencing portion of the tibial guide.

Referring to FIG. 9, resection guide portion 90 has a plurality of cut referencing surfaces, including a proximal cut slot 96, a medial cut slot 98 and a lateral cut slot 100, which together with a bottom surface of resection guide portion 90 define a trapezoidal peripheral shape. The trapezoidal peripheral shape formed by cut slots 96, 98, and 100 in turn defines the periphery of a tibial portion that is resected from tibia 10. Captured cut slots 96, 98 and 100 may guide an instrument such as reciprocating saw 102 (FIG. 10) to resect the tibial portion from tibia 10 along respective resection planes R1, R3 and R4. Alternatively, open planar cut referencing surfaces may be used along with, or instead of, the captured cut slots 96, 98, and 100.

Resection guide portion 90 includes apertures 88 as discussed above (FIGS. 8-11) and viewing window 104 to assist a surgeon with viewing the placement of guide 70 and/or providing an area on guide 70 for additional receipt of pins, such as pins 94 (FIG. 10), for example, to temporarily secure guide 70 to tibia 10. Pin holes or apertures 88, along with viewing window 104, are disposed within the periphery defined by cut slots 96, 98 and 100. Thus, as shown in FIG. 11 and described in the surgical technique below, when the tibial portion is resected from tibia 10, guide 70 and pins 94 are together removed with the resected tibial portion. In this manner, the pins used to temporarily secure guide 70 need not be placed in the non-resected portion of the distal tibia.

First portion 78 and second portion 80 of guide 70 conform and fit to distal tibia 10, as described above, such that slippage of guide 70 from distal tibia 10 is substantially prevented and, advantageously, a surgeon is provided with tactile feedback that guide 70 is properly positioned and oriented with respect to distal tibia 10. During the resection, saw 102 may cut through sections of referencing portion 74, which may be made of a resilient material such as plastic, for example, and/or may include metal inserts (not shown) for guidance of the saw blade.

2B. Talar Guide (FIGS. 7, 12-14)

Figure 7:
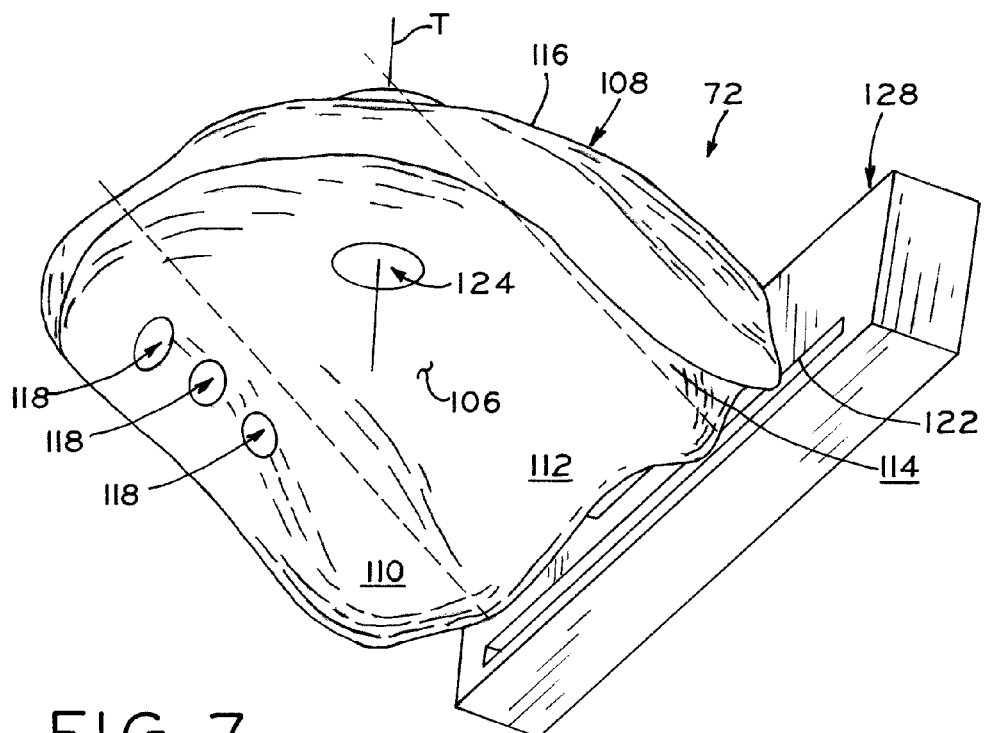
FIG. 7 is a distal perspective view of the talar guide, including a patient-specific referencing portion and a resection guide portion, the referencing portion having a reaming guide aperture and a distal patient-specific surface for conforming and seating to proximal surfaces of the talus, the resection guide portion including a cut slot.

Referring to FIGS. 7 and 12-14, an exemplary talar guide 72 of the orthopedic system includes a first, patient-specific referencing portion, which includes distal surface 106 that substantially conforms to and is a negative of surfaces and/or landmarks on the body of the talus along the proximal surface of the trochlea and the medial and lateral side edges of the trochlea. More specifically, referring to FIGS. 7 and 12-14, patient-specific referencing portion 108 of talar guide 72 includes first, second, and third portions 110, 112 and 114 (FIG. 7), proximal surface 116 (FIG. 12), and distal surface 106 (FIG. 7).

Figure 13:
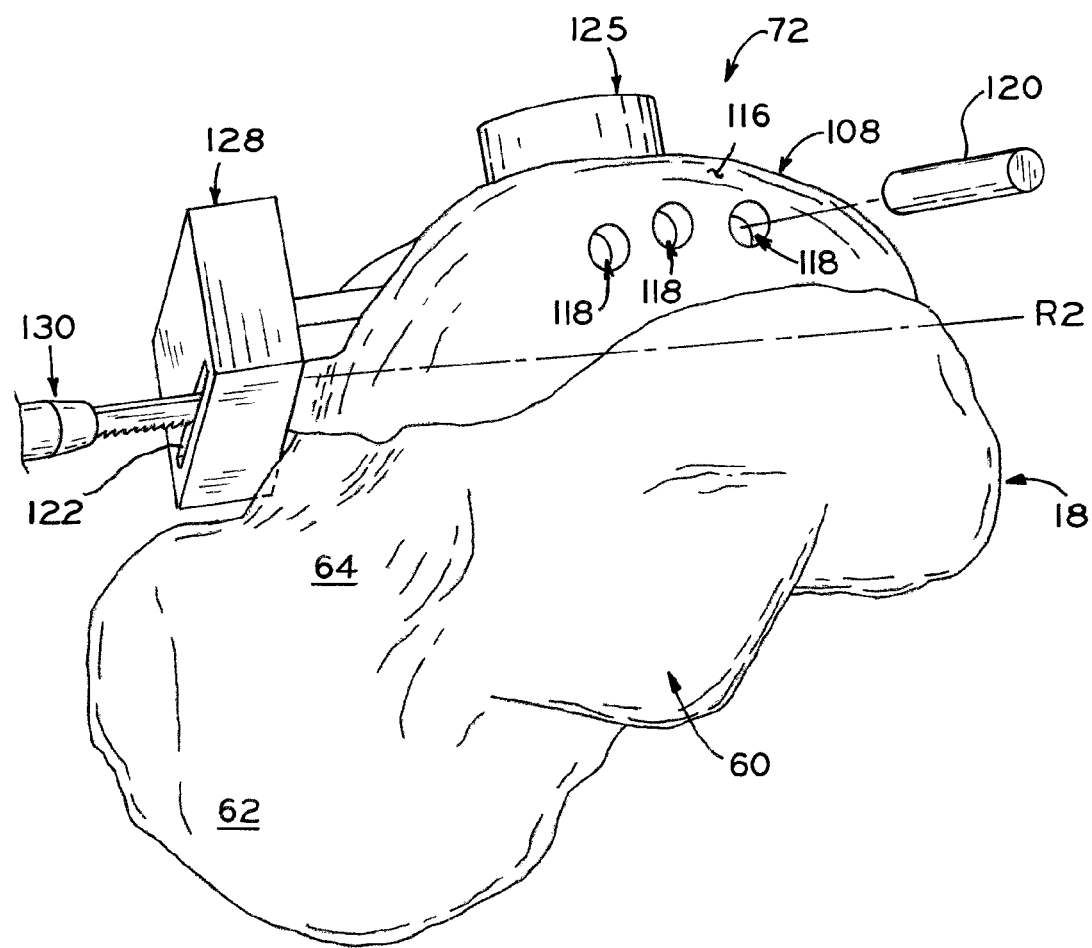
FIG. 13 is a lateral perspective view of the talar guide of FIG. 7 seated about a proximal surface of the talus, and an instrument guided via a cut slot on the resection guide portion to make a resection of the talus.

As shown in FIG. 7, first portion 110 of referencing portion 108 is disposed on the lateral end of referencing portion 108 and includes apertures 118 for receipt of pins, such as pin 120 (FIG. 13) for example, to temporarily secure guide 72 to talus 18. Pin holes or apertures 118 are disposed proximally or above the resection plane defined by cut slot 122 (described further below) such that when the resected talar portion is removed from talus 18, guide 72 and pins 120 are removed with the resected portion. In this manner, the pins used to temporarily secure guide 72 need not be placed in the non-resected portion of the distal tibia. Thus, as shown in FIG. 13, apertures 118 are disposed proximal to cutting surface 122 that defines resection plane R2. First portion 110 of referencing portion 108 includes the portion of distal surface 106 of referencing portion 108 that substantially conforms to and is a negative of selected regions or portions of lateral side edge 56 and proximal surface 51 of trochlea 50.

Referring back to FIG. 7, second portion 112 of referencing portion 108 is disposed centrally, or intermediate the lateral and medial ends of referencing portion 108. Second portion 112 of referencing portion 108 includes the portion of distal surface 106 of referencing portion 108 that substantially conforms to and is a negative of selected regions or portions of proximal surface 51 of trochlea 50. Second portion 112 of referencing portion 108 includes reaming guide aperture 124 extending between proximal surface 116 and distal surface 106 of referencing portion 108. Reaming guide aperture 124 may optionally be formed through a boss 125 (FIG. 12) proximally extending from proximal surface 116 of referencing portion 108.

Guide aperture 124 of referencing portion 108 is designed based on patient-specific imaging data to align with, or be angled at a pre-determined angle from, the anatomical axis T of distal tibia 10 when referencing portion 108 is seated against talus 18. Guide aperture 124 of referencing portion 108 may guide an instrument such as reamer 126 (FIG. 12) to ream a talar canal, as described further below.

Third portion 114 of referencing portion 108 is disposed on the medial end of referencing portion 108. Third portion 114 of referencing portion 108 includes the portion of distal surface 106 of referencing portion 108 that substantially conforms to and is a negative of selected regions or portions of medial side edge 54 and proximal surface 51 of trochlea 50.

As described above, medial side edge 54 and lateral side edge 56 of trochlea 50 inwardly taper with respect to one another along an anterior to posterior direction. When referencing portion 108 connects to and conforms with selected regions of talus 18 via first, second, and third portions 110, 112, and 114, respectively, as described above, referencing portion 108 forms a tapered locking fit connection with talus 18. Particularly, first portion 110 and third portion 114 conform to selected regions of and about lateral side edge 56 and medial side edge 54, respectively, of trochlea 50 to wrap around the edges and form the tapered lock, which connects guide 72 to talus 18 to conformingly locate and position guide 72 with respect to talus 18. Thus, advantageously, slippage of guide 72 from talus 18 is substantially prevented and a surgeon is provided with tactile feedback that guide 72 is properly positioned and oriented with respect to talus 18.

Referencing portion 108 is connected to second, resection guide portion 128, which may be integral with or modular and separately attached to referencing portion 108. Resection guide portion 128 includes a cut referencing surface such as cut slot 122 to resect a portion from talus 18 along resection plane R2 via an instrument such as reciprocating saw 130 (FIG. 13). Referring to FIG. 14, during the resection, saw 130 may cut through sections of referencing portion 108, which may be made of a resilient material such as plastic, for example, and/or may include metal inserts (not shown) for guiding the saw blade.

3. Surgical Technique

At the beginning of the surgical procedure, the surgeon accesses at least one of talus 18 and a distal end of tibia 10, optionally using a minimally invasive surgical procedure and, if necessary, the surgeon moves the trochlea region of talus 18 away from distal tibia 10.

After talus 18 and distal tibia 10 are exposed, the surgeon places the respective talar or tibial patient-specific guide against talus 18 or tibia 10. While the surgeon may elect to first operate on distal tibia 10 prior to talus 18 as described below, the reverse is possible.

The tibial and talar guides described throughout may be modified to include additional structures such as pin placer holes, drill guides, linked cut guides, and adjustable cut or drill guides, for example. Also, the tibial and talar guides may include navigation, orientation, and/or position sensor devices to allow modification of the guides themselves and/or to allow adjustability of the guides during use. Further, the tibial and talar guides may be modified to provide instrumentation for implanting the ankle implants described in U.S. Pat. No. 7,625,409 or U.S. Patent Application Publication No. 2005/0004676, both of which were previously incorporated herein by reference.

3A. Surgical Technique for the Tibia

Figure 10:
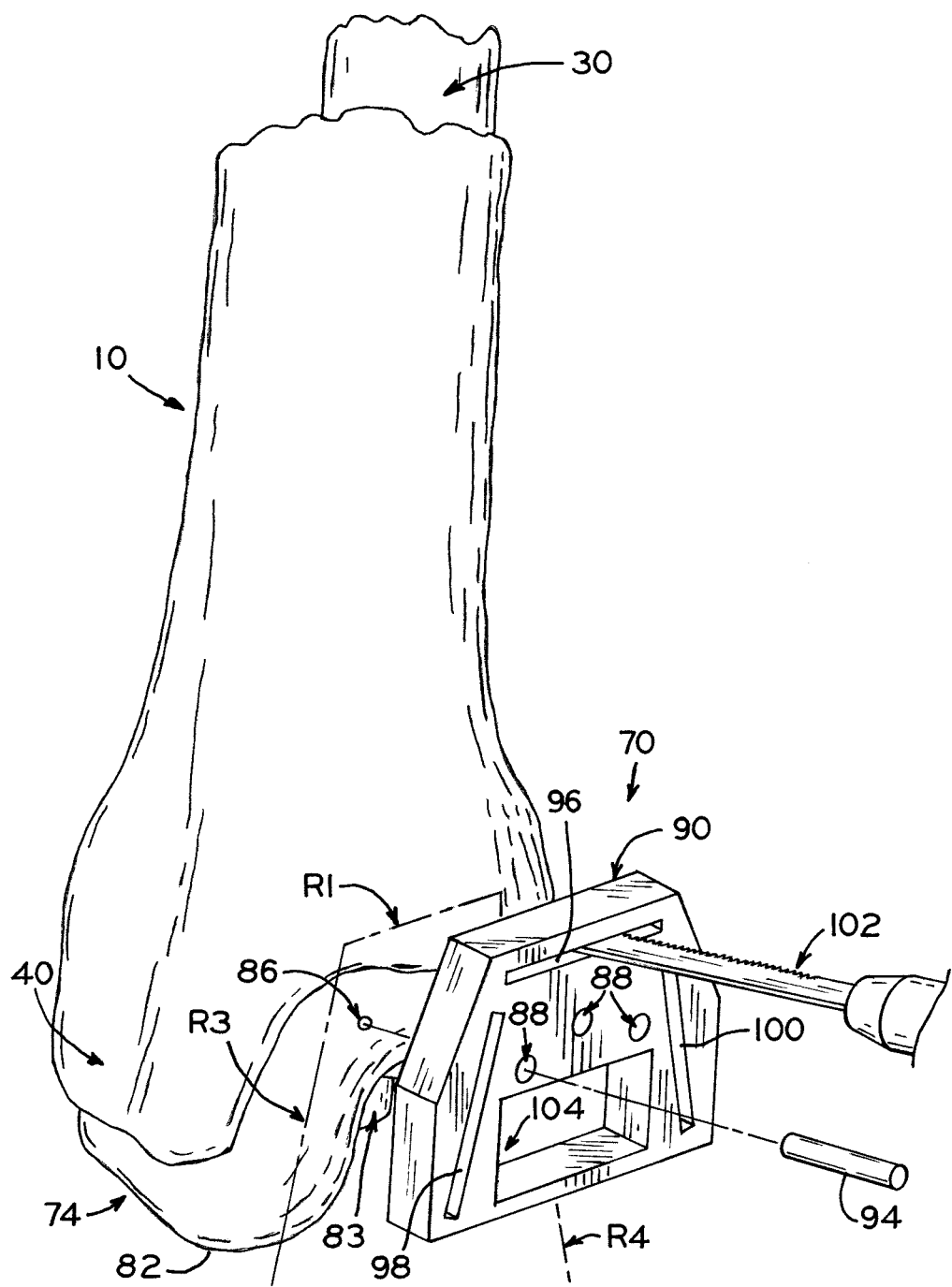
FIG. 10 is a medial perspective view of the tibial guide of FIG. 8 seated on the distal tibia, showing an instrument guided via cut slots on the resection guide portion to make resections along illustrated resection planes.
Figure 11:
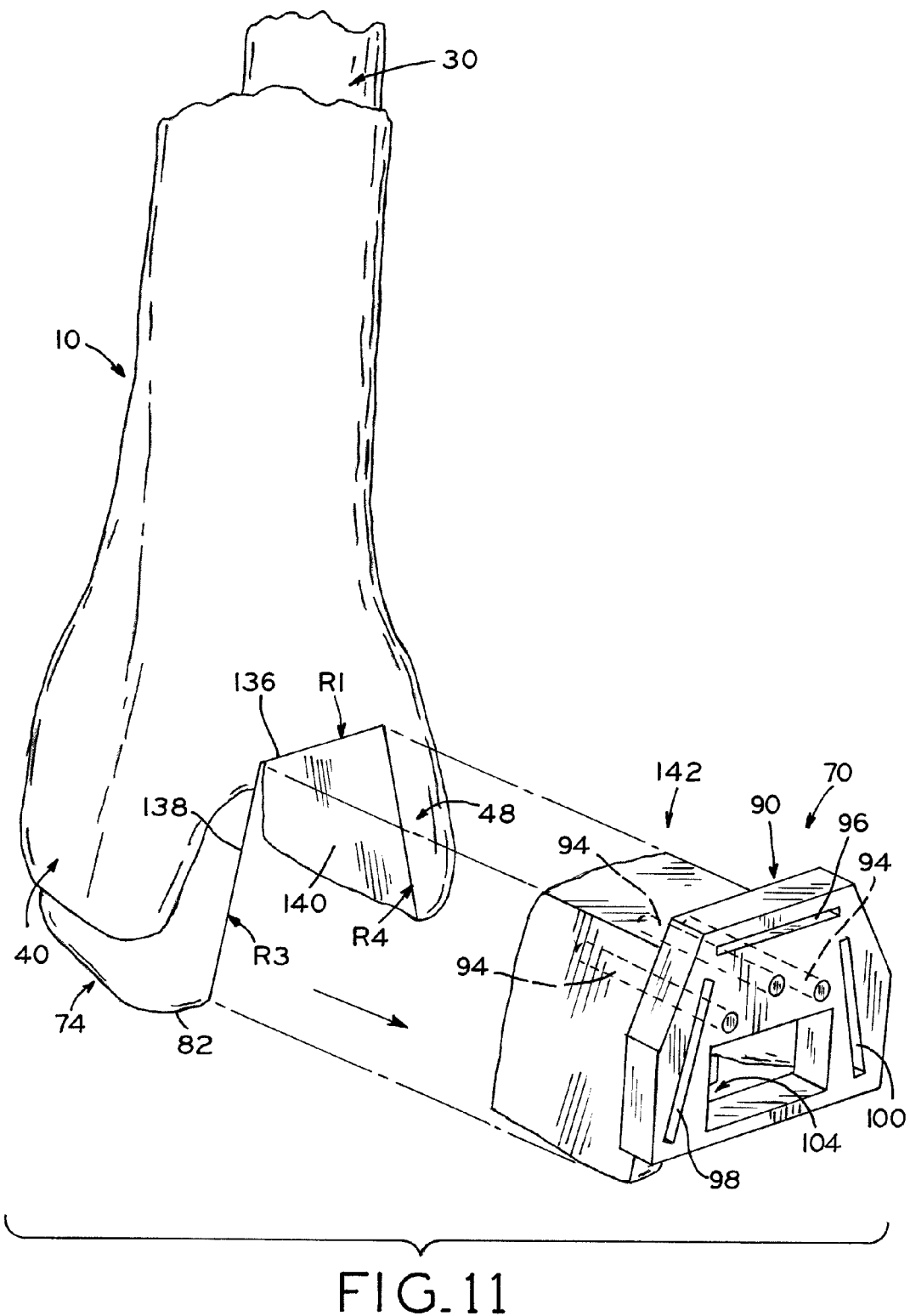
FIG. 11 is a medial perspective view of the tibial guide of FIG. 8 being removed along with a resected portion of the distal tibia after performing the resection.

During the tibial procedure, described in further detail below, the surgeon will place tibial guide 70 on distal tibia 10 and secure guide 70 to distal tibia 10 via pins 94 (FIG. 10). Next, the surgeon will ream distal tibia 10 along anatomical axis T via guide aperture 84 that guides reamer 85 (FIG. 9) to form canal 132. Then, the surgeon will resect a tibial portion of distal tibia 10 via cut slots 96, 98, 100 along resection planes R1, R3 and R4 (FIG. 10), respectively, such that guide 70 and securement pins 94 (FIG. 11) are removed along with the tibial portion of resected bone, as described below.

Figure 6:
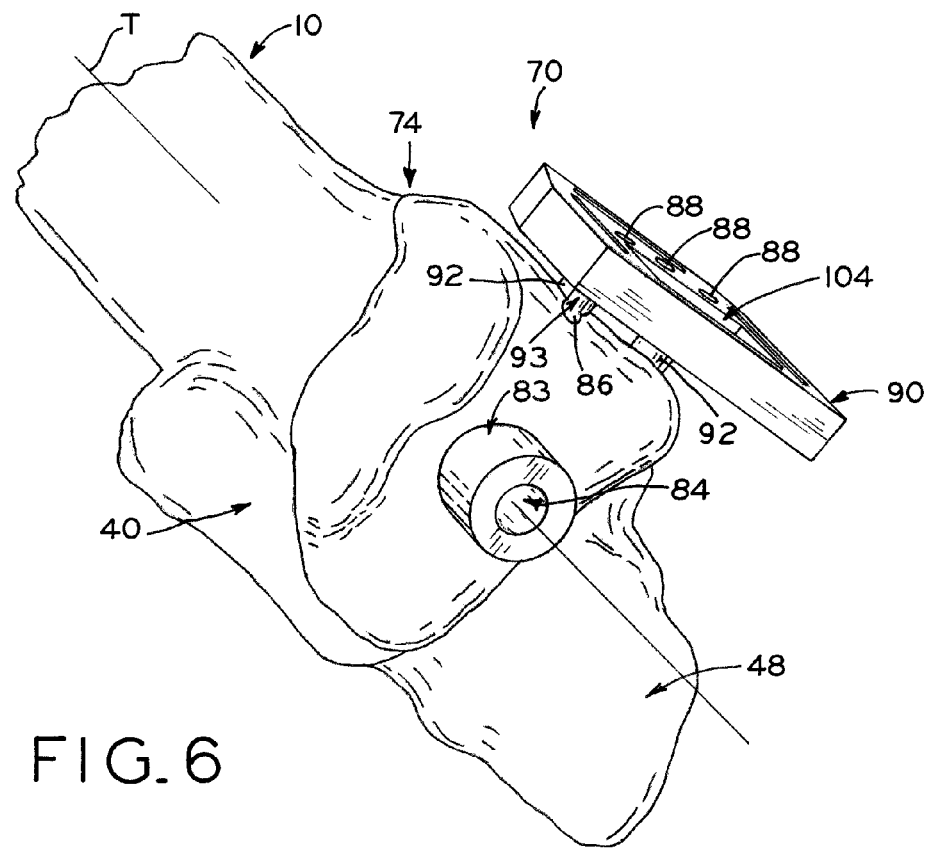
FIG. 6 is a distal perspective view of the tibial guide, including a patient-specific referencing portion and a resection guide portion, the referencing portion seated about portions of the distal surfaces of the distal tibia and having a reaming guide aperture aligned with the anatomical tibial axis.

First, the surgeon orients tibial patient-specific guide 70 with a proximal surface of the guide facing toward tibia 10 and a distal surface of the guide facing away from tibia 10, as shown in FIGS. 6 and 10. According to an exemplary embodiment of the present disclosure, the tibial patient-specific guide conforms to tibia 10 at predetermined locations. For example, a proximal surface of the guide may be shaped to match the contour of tibia 10 at respective predetermined locations of a distal portion of tibia 10.

Once the tibial guide is properly aligned with and seated on tibia 10, respectively, the surgeon may temporarily secure the respective guide to tibia 10. For example, the surgeon may temporarily secure tibial guide 70 to tibia 10 by inserting screws, pins, or other suitable anchors, such as pin 94 of FIG. 10, through apertures 86 and 88 in guide 70 and into the bone of tibia 10. Any suitable number and arrangement of apertures may be provided in tibial guide 70.

The surgeon may then use the tibial bone canal preparation reaming guide 84, shown in FIG. 9, to ream a distal tibial canal along the tibial anatomical axis T. For example, the surgeon may prepare the tibial canal via reamers of progressively increasing diameter that are utilized to ream the tibial canal to achieve an optimal fit for the prosthesis to be seated within the prepared tibial canal. Thus, during the procedure, tibial guide 70 (FIGS. 6, 8-11) controls the position of a reaming tool such as reamer 85 (FIG. 9) relative to tibia 10 so that the reaming tool removes a desired portion of cancellous bone from tibia 10.

An exemplary tibial guide may include other features for preparing tibia 10 to receive a distal tibial prosthesis. For example, it is within the scope of the present disclosure that tibial guide 70 may include holes for drilling anchor holes into tibia 10.

Next, the surgeon uses tibial patient-specific guide 70 (discussed above) to resect and prepare distal tibia 10. Tibial guide 70 (FIGS. 6, 8-11) provides one or more cut guide slots to guide a saw that resects a first portion of the distal tibia from the body along predetermined angles and positions. For example, referring to FIG. 11, the surgeon may use a saw blade of reciprocating saw 102 (FIG. 10) to resect a tibial portion from distal tibia 10 along proximal cut slot 96 of guide 70 to form internal distal resection 136 along resection plane R1, along medial cut slot 98 of guide 70 to form internal medial resection 138 along resection plane R3, and along lateral cut slot 100 of guide 70 to form internal lateral resection 140 along resection plane R4. It is also within the scope of the present disclosure that the tibial guide may be provided with other cut referencing surfaces or cut slots so that the surgeon is able to cut other surfaces of the tibia at predetermined locations.

3B. Surgical Technique for the Talus

Figure 12:
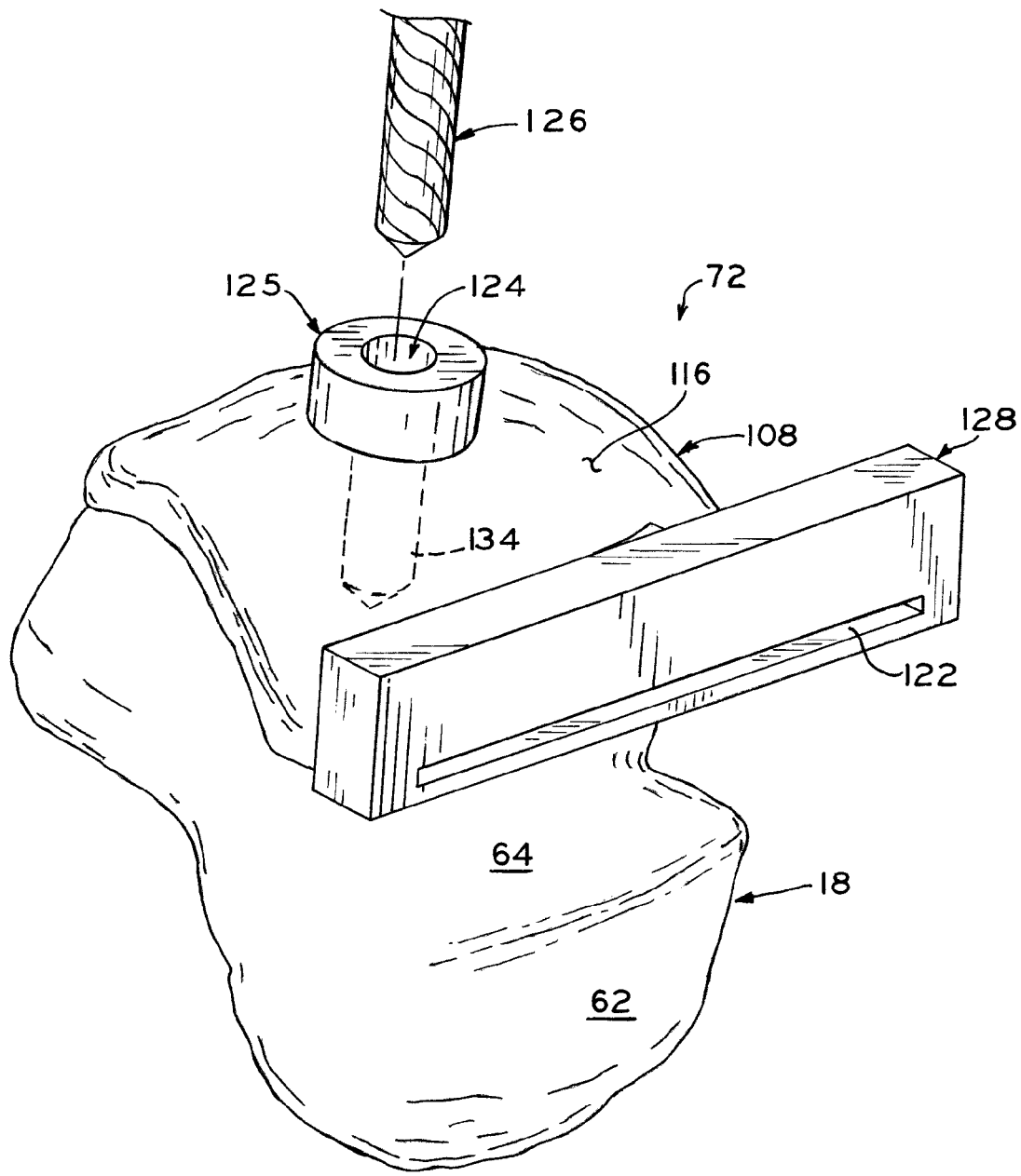
FIG. 12 is a medial perspective view of the exemplary talar guide of FIG. 7 seated about a proximal surface of the talus.

The surgeon will place talar guide 72 on talus 18 via pins 120 (FIG. 13), for example. Next, the surgeon will ream a talar canal or bore 134 (FIG. 12) along or angled with respect to the above-referenced pre-determined anatomical axis T of the tibia 10 via reamer 126 (FIG. 12). The surgeon will then resect a portion of the talus 18 via cutting surface 122 along resection plane R2 (FIG. 13) such that the securement pins 120 (FIG. 14) and guide 72 are removed along with the portion of resected bone, as described below.

In particular, the surgeon first orients the talar patient-specific guide 72 with a distal surface of the guide facing towards talus 18 and a proximal surface of the guide facing away from talus 18, as shown in FIGS. 12 and 13. Once the talar guide is properly aligned with talus 18, the surgeon may temporarily secure the respective guide to talus 18 by inserting screws, pins, or other suitable anchors through apertures of the guide and into the bone. For example, the surgeon may temporarily secure talar guide 72 to talus 18 via the insertion of pins 120 (FIG. 13) through apertures 118 and into the bone of talus 18.

Additionally, talar guide 72 may include other features for preparing the talus to seat and receive a talar prosthesis. Talar guide 72 may receive a reamer, such as reamer 126 (FIG. 12), that prepares the talus to receive a talar prosthesis via reaming a talar canal or bore aligned with or angled with respect to the anatomical axis of the distal tibia. During the procedure, talar guide 72 (FIGS. 7, 12-14) controls the position of a reaming tool such as reamer 126 (FIG. 12) relative to talus 18 so that the reaming tool removes a desired talus portion 144 of cancellous bone from talus 18 as shown in FIG. 14.

Next, the surgeon uses the talar patient-specific guide (discussed above) to resect and prepare talus 18. Talar guide 72 (FIGS. 7, 12-14) provides one or more cut guide slots to guide a saw that resects a portion of the talus from the body along predetermined angles and positions.

The surgeon may use guide 72, for example, and reciprocating saw 130 (FIG. 13) to cut portions of talus 18. For example, the surgeon may use a saw blade of reciprocating saw 130 (FIG. 13) along proximal cut slot 122 of guide 72 to resect a portion of talus 18 along predetermined cut lines such as resection plane R2. It is also within the scope of the present disclosure that talar guide 72 may be provided with other cut referencing surfaces or cut slots so that the surgeon is able to cut other surfaces of the talus at predetermined locations.

3C. Surgical Technique for Implanting the Prostheses

After preparing talus 18 and/or tibia 10, the desired prostheses are implanted. Providing the desired prostheses may involve obtaining manufactured custom, patient-specific prostheses based on the patient-specific prostheses designed during step 505A of method 500 (FIG. 5). Alternatively, providing the desired prostheses may involve choosing standard prostheses from a set of known orthopedic prostheses as set forth during step 505B of method 500 (FIG. 5).

According to an exemplary embodiment of the present disclosure, a patient-specific distal tibial prosthesis may be provided that is sized and shaped to replicate the portion of bone that was removed from tibia 10 using tibial guide 70. However, if the natural articulating surface of tibia 10 had been damaged or had deteriorated, the patient-specific distal tibial prosthesis may be sized and shaped to replicate the portion of bone that was removed from tibia 10 using tibial guide 70, as well as the portion of bone that was missing from tibia 10 due to disease or traumatic injury, for example.

According to another exemplary embodiment of the present disclosure, a patient-specific talar prosthesis may be similarly provided to be sized and shaped to replicate the portion of bone removed from the talus 18 using guide 72, for example, and to have an articulating surface for indirect or direct articulation with the articulating surface of the distal tibial prosthesis.

Finally, the surgeon implants the desired distal tibial prosthesis in distal tibia 10 and/or the desired talar prosthesis in talus 18, as shown in FIG. 15 and described above.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A tibial guide for preparing a distal tibia to receive a prosthesis, said tibial guide comprising:

a body having a first portion and a second portion, the first portion including a patient-specific surface being contoured to rest against and conform to one or more portions of at least one of an articular capsule, an anterior protrusion, and a medial malleolus of the distal tibia, said second portion including a first and at least a second cut referencing surface configured to guide a cutting instrument for performing a resection, the first cut referencing surface and the at least a second cut referencing surface being disposed at an angle with respect to one another to together define a resection periphery on the second portion of the body, the first portion and the second portion being connected by at least one shaft such that when the patient-specific surface of the first portion rests against and conforms to the one or more portions of the at least one of the articular capsule, the anterior protrusion, and the medial malleolus of the distal tibia, the second portion is disposed anteriorly of the distal tibia such that the resection is performed anteriorly; and at least one enclosed pin aperture in said body, each of the at least one pin aperture configured to receive a pin for securing said tibial guide against the distal tibia, said at least one pin aperture being disposed exclusively within the resection periphery of the second portion of the body while a remainder of the second portion of the body outside said resection periphery is free of pin apertures, the resection periphery of the body corresponding to a resection portion of the distal tibia, wherein each pin respectively received through said at least one pin aperture is also disposed within said resection periphery of the body and said resection portion of the distal tibia, whereby when the resection is performed and the resection portion of the distal tibia is removed, the tibial guide and each pin are removed along with the resection portion of the distal tibia.

2. The tibial guide of claim 1, wherein said patient-specific surface is contoured to rest against and conform to one or more portions of the anterior protrusion and the medial malleolus of the distal tibia.

3. The tibial guide of claim 1, wherein said first portion further includes a guide aperture configured to guide a reaming instrument.

4. The tibial guide of claim 1, wherein said first cut referencing surface, when said tibial guide is conformingly positioned against the distal tibia, is disposed perpendicularly to an anatomical axis of the tibia.

5. The tibial guide of claim 1, wherein said resection periphery has a trapezoidal shape defining a trapezoidal periphery of the resection portion of the distal tibia.

6. A patient-specific guide for guiding an instrument to resect a resection portion of a bone to prepare the bone to receive a prosthesis, said guide comprising:

a body having a patient-specific referencing portion and a resection guide portion, said patient-specific referencing portion including at least one patient-specific surface being contoured to rest against and conform to a surface of the bone, said resection guide portion including at least first and second cut referencing surfaces together defining a resection periphery on the resection guide portion of the body, the resection periphery of the body corresponding to the resection portion of the bone, wherein the bone is a distal tibia, said first cut referencing surface being oriented perpendicularly to a tibial anatomical axis when said at least one patient-specific surface is conformingly positioned against the bone;

a guide aperture configured to guide a reaming instrument, the guide aperture extending through said patient-specific surface such that the reaming instrument extends through the guide aperture along the tibial anatomical axis of the bone and perpendicular to the first cut referencing surface when the at least one patient-specific surface is conformingly positioned against the bone; and said body further including at least one enclosed pin aperture disposed in said resection guide portion, each of said at least one enclosed pin aperture being disposed exclusively within the resection periphery of the resection guide portion of the body while a remainder of the resection guide portion of the body outside said resection periphery is free of pin apertures, each of said at least one enclosed pin aperture dimensioned to receive a pin to secure said guide to the bone, whereby when the resection is performed and the resection portion of the bone is removed, the guide and each pin are removed along with the resection portion of the bone.

7. The guide of claim 6, wherein the resection periphery has a trapezoidal shape.

8. The guide of claim 6, wherein said at least one patient-specific surface is contoured to rest against and conform to one or more portions of an anterior protrusion and a medial malleolus of the distal tibia.

* * * * *